US012599445B2

(12) United States Patent
Sage et al.

(10) Patent No.: US 12,599,445 B2
(45) Date of Patent: Apr. 14, 2026

(54) SURGICAL ROBOTIC SYSTEM AND METHOD FOR CART POWER SWITCHOVER

(71) Applicant: Covidien LP, Mansfield, MA (US)

(72) Inventors: Lawrence A. Sage, Killingworth, CT (US); Gary P. Beck, East Hampton, CT (US)

(73) Assignee: Covidien LP, Mansfield, MA (US)

( * ) Notice: Subject to any disclaimer, the term of this patent is extended or adjusted under 35 U.S.C. 154(b) by 142 days.

(21) Appl. No.: 18/407,575

(22) Filed: Jan. 9, 2024

(65) Prior Publication Data

US 2024/0252261 A1     Aug. 1, 2024

Related U.S. Application Data

(60) Provisional application No. 63/441,221, filed on Jan. 26, 2023.

(51) Int. Cl.
| | |
|---|---|
| *A61B 34/35* | (2016.01) |
| *A61B 17/00* | (2006.01) |
| *A61B 34/00* | (2016.01) |
| *A61B 34/30* | (2016.01) |
| *A61B 50/13* | (2016.01) |

(52) U.S. Cl.
CPC .............. *A61B 34/30* (2016.02); *A61B 17/00* (2013.01); *A61B 34/25* (2016.02); *A61B 50/13* (2016.02); *A61B 2017/00734* (2013.01); *A61B 2034/305* (2016.02)

(58) Field of Classification Search
USPC .............................. 700/245–264; 606/1, 130
See application file for complete search history.

(56) References Cited

U.S. PATENT DOCUMENTS

| | | | |
|---|---|---|---|
| 6,132,368 | A | 10/2000 | Cooper |
| 6,206,903 | B1 | 3/2001 | Ramans |
| 6,246,200 | B1 | 6/2001 | Blumenkranz et al. |
| 6,312,435 | B1 | 11/2001 | Wallace et al. |
| 6,331,181 | B1 | 12/2001 | Tierney et al. |
| 6,394,998 | B1 | 5/2002 | Wallace et al. |

(Continued)

FOREIGN PATENT DOCUMENTS

| | | | | |
|---|---|---|---|---|
| EP | 4154835 | A1 * | 3/2023 | ............. A61B 34/37 |
| GB | 2594327 | A * | 10/2021 | ............. A61B 34/25 |

(Continued)

*Primary Examiner* — Jonathan L Sample

(74) *Attorney, Agent, or Firm* — Carter, DeLuca & Farrel

(57) ABSTRACT

A power delivery system for a surgical robotic movable cart includes a power input configured to receive a first DC electrical signal, a first voltage sense and control circuit coupled to the power input and operable in a primary power mode to output the first DC electrical signal, and a battery configured to output a second DC electrical signal. The system also includes a battery charging circuit configured to receive the first DC electrical signal and to charge the battery, and a second voltage sense and control circuit coupled to the battery and operable in a battery power mode to output the second DC electrical signal. The system further includes a sharing circuit configured to output at least one of the first DC electrical signal from the first voltage sense and control circuit or the second DC electrical signal from the second voltage sense and control circuit.

13 Claims, 7 Drawing Sheets

(56) References Cited

U.S. PATENT DOCUMENTS

| | | | |
|---|---|---|---|
| 6,424,885 B1 | 7/2002 | Niemeyer et al. |
| 6,441,577 B2 | 8/2002 | Blumenkranz et al. |
| 6,459,926 B1 | 10/2002 | Nowlin et al. |
| 6,491,691 B1 | 12/2002 | Morley et al. |
| 6,491,701 B2 | 12/2002 | Tierney et al. |
| 6,493,608 B1 | 12/2002 | Niemeyer |
| 6,565,554 B1 | 5/2003 | Niemeyer |
| 6,645,196 B1 | 11/2003 | Nixon et al. |
| 6,659,939 B2 | 12/2003 | Moll |
| 6,671,581 B2 | 12/2003 | Niemeyer et al. |
| 6,676,684 B1 | 1/2004 | Morley et al. |
| 6,685,698 B2 | 2/2004 | Morley et al. |
| 6,699,235 B2 | 3/2004 | Wallace et al. |
| 6,714,839 B2 | 3/2004 | Salisbury, Jr. et al. |
| 6,716,233 B1 | 4/2004 | Whitman |
| 6,728,599 B2 | 4/2004 | Wang et al. |
| 6,746,443 B1 | 6/2004 | Morley et al. |
| 6,766,204 B2 | 7/2004 | Niemeyer et al. |
| 6,770,081 B1 | 8/2004 | Cooper et al. |
| 6,772,053 B2 | 8/2004 | Niemeyer |
| 6,783,524 B2 | 8/2004 | Anderson et al. |
| 6,793,652 B1 | 9/2004 | Whitman et al. |
| 6,793,653 B2 | 9/2004 | Sanchez et al. |
| 6,799,065 B1 | 9/2004 | Niemeyer |
| 6,837,883 B2 | 1/2005 | Moll et al. |
| 6,839,612 B2 | 1/2005 | Sanchez et al. |
| 6,840,938 B1 | 1/2005 | Morley et al. |
| 6,843,403 B2 | 1/2005 | Whitman |
| 6,846,309 B2 | 1/2005 | Whitman et al. |
| 6,866,671 B2 | 3/2005 | Tierney et al. |
| 6,871,117 B2 | 3/2005 | Wang et al. |
| 6,879,880 B2 | 4/2005 | Nowlin et al. |
| 6,899,705 B2 | 5/2005 | Niemeyer |
| 6,902,560 B1 | 6/2005 | Morley et al. |
| 6,936,042 B2 | 8/2005 | Wallace et al. |
| 6,951,535 B2 | 10/2005 | Ghodoussi et al. |
| 6,974,449 B2 | 12/2005 | Niemeyer |
| 6,991,627 B2 | 1/2006 | Madhani et al. |
| 6,994,708 B2 | 2/2006 | Manzo |
| 7,048,745 B2 | 5/2006 | Tierney et al. |
| 7,066,926 B2 | 6/2006 | Wallace et al. |
| 7,118,582 B1 | 10/2006 | Wang et al. |
| 7,125,403 B2 | 10/2006 | Julian et al. |
| 7,155,315 B2 | 12/2006 | Niemeyer et al. |
| 7,239,940 B2 | 7/2007 | Wang et al. |
| 7,306,597 B2 | 12/2007 | Manzo |
| 7,357,774 B2 | 4/2008 | Cooper |
| 7,373,219 B2 | 5/2008 | Nowlin et al. |
| 7,379,790 B2 | 5/2008 | Toth et al. |
| 7,386,365 B2 | 6/2008 | Nixon |
| 7,391,173 B2 | 6/2008 | Schena |
| 7,398,707 B2 | 7/2008 | Morley et al. |
| 7,413,565 B2 | 8/2008 | Wang et al. |
| 7,453,227 B2 | 11/2008 | Prisco et al. |
| 7,524,320 B2 | 4/2009 | Tierney et al. |
| 7,574,250 B2 | 8/2009 | Niemeyer |
| 7,594,912 B2 | 9/2009 | Cooper et al. |
| 7,607,440 B2 | 10/2009 | Coste-Maniere et al. |
| 7,666,191 B2 | 2/2010 | Orban, III et al. |
| 7,682,357 B2 | 3/2010 | Ghodoussi et al. |
| 7,689,320 B2 | 3/2010 | Prisco et al. |
| 7,695,481 B2 | 4/2010 | Wang et al. |
| 7,695,485 B2 | 4/2010 | Whitman et al. |
| 7,699,855 B2 | 4/2010 | Anderson et al. |
| 7,713,263 B2 | 5/2010 | Niemeyer |
| 7,725,214 B2 | 5/2010 | Diolaiti |
| 7,727,244 B2 | 6/2010 | Orban, III et al. |
| 7,741,802 B2 | 6/2010 | Prisco |
| 7,756,036 B2 | 7/2010 | Druke et al. |
| 7,757,028 B2 | 7/2010 | Druke et al. |
| 7,762,825 B2 | 7/2010 | Burbank et al. |
| 7,778,733 B2 | 8/2010 | Nowlin et al. |
| 7,803,151 B2 | 9/2010 | Whitman |
| 7,806,891 B2 | 10/2010 | Nowlin et al. |
| 7,819,859 B2 | 10/2010 | Prisco et al. |
| 7,819,885 B2 | 10/2010 | Cooper |
| 7,824,401 B2 | 11/2010 | Manzo et al. |
| 7,835,823 B2 | 11/2010 | Sillman et al. |
| 7,843,158 B2 | 11/2010 | Prisco |
| 7,865,266 B2 | 1/2011 | Moll et al. |
| 7,865,269 B2 | 1/2011 | Prisco et al. |
| 7,886,743 B2 | 2/2011 | Cooper et al. |
| 7,899,578 B2 | 3/2011 | Prisco et al. |
| 7,907,166 B2 | 3/2011 | Lamprecht et al. |
| 7,935,130 B2 | 5/2011 | Williams |
| 7,963,913 B2 | 6/2011 | Devengenzo et al. |
| 7,983,793 B2 | 7/2011 | Toth et al. |
| 8,002,767 B2 | 8/2011 | Sanchez |
| 8,004,229 B2 | 8/2011 | Nowlin et al. |
| 8,012,170 B2 | 9/2011 | Whitman et al. |
| 8,054,752 B2 | 11/2011 | Druke et al. |
| 8,062,288 B2 | 11/2011 | Cooper et al. |
| 8,079,950 B2 | 12/2011 | Stern et al. |
| 8,100,133 B2 | 1/2012 | Mintz et al. |
| 8,108,072 B2 | 1/2012 | Zhao et al. |
| 8,120,301 B2 | 2/2012 | Goldberg et al. |
| 8,142,447 B2 | 3/2012 | Cooper et al. |
| 8,147,503 B2 | 4/2012 | Zhao et al. |
| 8,151,661 B2 | 4/2012 | Schena et al. |
| 8,155,479 B2 | 4/2012 | Hoffman et al. |
| 8,182,469 B2 | 5/2012 | Anderson et al. |
| 8,202,278 B2 | 6/2012 | Orban, III et al. |
| 8,206,406 B2 | 6/2012 | Orban, III |
| 8,210,413 B2 | 7/2012 | Whitman et al. |
| 8,216,250 B2 | 7/2012 | Orban, III et al. |
| 8,220,468 B2 | 7/2012 | Cooper et al. |
| 8,256,319 B2 | 9/2012 | Cooper et al. |
| 8,285,517 B2 | 10/2012 | Sillman et al. |
| 8,315,720 B2 | 11/2012 | Mohr et al. |
| 8,335,590 B2 | 12/2012 | Costa et al. |
| 8,347,757 B2 | 1/2013 | Duval |
| 8,374,723 B2 | 2/2013 | Zhao et al. |
| 8,418,073 B2 | 4/2013 | Mohr et al. |
| 8,419,717 B2 | 4/2013 | Diolaiti et al. |
| 8,423,182 B2 | 4/2013 | Robinson et al. |
| 8,452,447 B2 | 5/2013 | Nixon |
| 8,454,585 B2 | 6/2013 | Whitman |
| 8,499,992 B2 | 8/2013 | Whitman et al. |
| 8,508,173 B2 | 8/2013 | Goldberg et al. |
| 8,528,440 B2 | 9/2013 | Morley et al. |
| 8,529,582 B2 | 9/2013 | Devengenzo et al. |
| 8,540,748 B2 | 9/2013 | Murphy et al. |
| 8,551,116 B2 | 10/2013 | Julian et al. |
| 8,562,594 B2 | 10/2013 | Cooper et al. |
| 8,594,841 B2 | 11/2013 | Zhao et al. |
| 8,597,182 B2 | 12/2013 | Stein et al. |
| 8,597,280 B2 | 12/2013 | Cooper et al. |
| 8,600,551 B2 | 12/2013 | Itkowitz et al. |
| 8,608,773 B2 | 12/2013 | Tierney et al. |
| 8,620,473 B2 | 12/2013 | Diolaiti et al. |
| 8,624,537 B2 | 1/2014 | Nowlin et al. |
| 8,634,957 B2 | 1/2014 | Toth et al. |
| 8,638,056 B2 | 1/2014 | Goldberg et al. |
| 8,638,057 B2 | 1/2014 | Goldberg et al. |
| 8,644,988 B2 | 2/2014 | Prisco et al. |
| 8,666,544 B2 | 3/2014 | Moll et al. |
| 8,668,638 B2 | 3/2014 | Donhowe et al. |
| 8,746,252 B2 | 6/2014 | McGrogan et al. |
| 8,749,189 B2 | 6/2014 | Nowlin et al. |
| 8,749,190 B2 | 6/2014 | Nowlin et al. |
| 8,758,352 B2 | 6/2014 | Cooper et al. |
| 8,761,930 B2 | 6/2014 | Nixon |
| 8,768,516 B2 | 7/2014 | Diolaiti et al. |
| 8,786,241 B2 | 7/2014 | Nowlin et al. |
| 8,790,243 B2 | 7/2014 | Cooper et al. |
| 8,808,164 B2 | 8/2014 | Hoffman et al. |
| 8,816,628 B2 | 8/2014 | Nowlin et al. |
| 8,821,480 B2 | 9/2014 | Burbank |
| 8,823,308 B2 | 9/2014 | Nowlin et al. |
| 8,827,989 B2 | 9/2014 | Niemeyer |
| 8,838,270 B2 | 9/2014 | Druke et al. |
| 8,852,174 B2 | 10/2014 | Burbank |
| 8,858,547 B2 | 10/2014 | Brogna |
| 8,862,268 B2 | 10/2014 | Robinson et al. |

(56) References Cited

U.S. PATENT DOCUMENTS

| | | | |
|---|---|---|---|
| 8,864,751 B2 | 10/2014 | Prisco et al. | |
| 8,864,752 B2 | 10/2014 | Diolaiti et al. | |
| 8,903,546 B2 | 12/2014 | Diolaiti et al. | |
| 8,903,549 B2 | 12/2014 | Itkowitz et al. | |
| 8,911,428 B2 | 12/2014 | Cooper et al. | |
| 8,912,746 B2 | 12/2014 | Reid et al. | |
| 8,944,070 B2 | 2/2015 | Guthart | |
| 8,989,903 B2 | 3/2015 | Weir et al. | |
| 9,002,518 B2 | 4/2015 | Manzo | |
| 9,014,856 B2 | 4/2015 | Manzo et al. | |
| 9,016,540 B2 | 4/2015 | Whitman et al. | |
| 9,019,345 B2 | 4/2015 | O'Grady et al. | |
| 9,043,027 B2 | 5/2015 | Durant et al. | |
| 9,050,120 B2 | 6/2015 | Swarup et al. | |
| 9,055,961 B2 | 6/2015 | Manzo et al. | |
| 9,068,628 B2 | 6/2015 | Solomon et al. | |
| 9,078,684 B2 | 7/2015 | Williams | |
| 9,084,623 B2 | 7/2015 | Gomez et al. | |
| 9,095,362 B2 | 8/2015 | Dachs, II et al. | |
| 9,096,033 B2 | 8/2015 | Holop et al. | |
| 9,101,381 B2 | 8/2015 | Burbank et al. | |
| 9,113,877 B1 | 8/2015 | Whitman et al. | |
| 9,138,284 B2 | 9/2015 | Krom et al. | |
| 9,144,456 B2 | 9/2015 | Rosa et al. | |
| 9,198,730 B2 | 12/2015 | Prisco et al. | |
| 9,204,923 B2 | 12/2015 | Manzo et al. | |
| 9,226,648 B2 | 1/2016 | Saadat et al. | |
| 9,226,750 B2 | 1/2016 | Weir et al. | |
| 9,226,761 B2 | 1/2016 | Burbank | |
| 9,232,984 B2 | 1/2016 | Guthart et al. | |
| 9,241,766 B2 | 1/2016 | Duque et al. | |
| 9,241,767 B2 | 1/2016 | Prisco et al. | |
| 9,241,769 B2 | 1/2016 | Larkin et al. | |
| 9,259,275 B2 | 2/2016 | Burbank | |
| 9,259,277 B2 | 2/2016 | Rogers et al. | |
| 9,259,281 B2 | 2/2016 | Griffiths et al. | |
| 9,259,282 B2 | 2/2016 | Azizian et al. | |
| 9,261,172 B2 | 2/2016 | Solomon et al. | |
| 9,265,567 B2 | 2/2016 | Orban, III et al. | |
| 9,265,584 B2 | 2/2016 | Itkowitz et al. | |
| 9,283,049 B2 | 3/2016 | Diolaiti et al. | |
| 9,301,811 B2 | 4/2016 | Goldberg et al. | |
| 9,314,307 B2 | 4/2016 | Richmond et al. | |
| 9,317,651 B2 | 4/2016 | Nixon | |
| 9,345,546 B2 | 5/2016 | Toth et al. | |
| 9,393,017 B2 | 7/2016 | Flanagan et al. | |
| 9,402,689 B2 | 8/2016 | Prisco et al. | |
| 9,417,621 B2 | 8/2016 | Diolaiti | |
| 9,424,303 B2 | 8/2016 | Hoffman et al. | |
| 9,433,418 B2 | 9/2016 | Whitman et al. | |
| 9,446,517 B2 | 9/2016 | Burns et al. | |
| 9,452,020 B2 | 9/2016 | Griffiths et al. | |
| 9,474,569 B2 | 10/2016 | Manzo et al. | |
| 9,480,533 B2 | 11/2016 | Devengenzo et al. | |
| 9,503,713 B2 | 11/2016 | Zhao et al. | |
| 9,550,300 B2 | 1/2017 | Danitz et al. | |
| 9,554,859 B2 | 1/2017 | Nowlin et al. | |
| 9,566,124 B2 | 2/2017 | Prisco et al. | |
| 9,579,164 B2 | 2/2017 | Itkowitz et al. | |
| 9,585,641 B2 | 3/2017 | Cooper et al. | |
| 9,615,883 B2 | 4/2017 | Schena et al. | |
| 9,623,563 B2 | 4/2017 | Nixon | |
| 9,623,902 B2 | 4/2017 | Griffiths et al. | |
| 9,629,520 B2 | 4/2017 | Diolaiti | |
| 9,662,177 B2 | 5/2017 | Weir et al. | |
| 9,664,262 B2 | 5/2017 | Donlon et al. | |
| 9,675,354 B2 | 6/2017 | Weir et al. | |
| 9,680,333 B1 * | 6/2017 | Brooks | H02J 7/00714 |
| 9,687,312 B2 | 6/2017 | Dachs, II et al. | |
| 9,700,334 B2 | 7/2017 | Hinman et al. | |
| 9,718,190 B2 | 8/2017 | Larkin et al. | |
| 9,730,719 B2 | 8/2017 | Brisson et al. | |
| 9,737,199 B2 | 8/2017 | Pistor et al. | |
| 9,795,446 B2 | 10/2017 | DiMaio et al. | |
| 9,797,484 B2 | 10/2017 | Solomon et al. | |
| 9,801,690 B2 | 10/2017 | Larkin et al. | |
| 9,814,530 B2 | 11/2017 | Weir et al. | |
| 9,814,536 B2 | 11/2017 | Goldberg et al. | |
| 9,814,537 B2 | 11/2017 | Itkowitz et al. | |
| 9,820,823 B2 | 11/2017 | Richmond et al. | |
| 9,827,059 B2 | 11/2017 | Robinson et al. | |
| 9,830,371 B2 | 11/2017 | Hoffman et al. | |
| 9,839,481 B2 | 12/2017 | Blumenkranz et al. | |
| 9,839,487 B2 | 12/2017 | Dachs, II | |
| 9,850,994 B2 | 12/2017 | Schena | |
| 9,855,102 B2 | 1/2018 | Blumenkranz | |
| 9,855,107 B2 | 1/2018 | Labonville et al. | |
| 9,872,737 B2 | 1/2018 | Nixon | |
| 9,877,718 B2 | 1/2018 | Weir et al. | |
| 9,883,920 B2 | 2/2018 | Blumenkranz | |
| 9,888,974 B2 | 2/2018 | Niemeyer | |
| 9,895,813 B2 | 2/2018 | Blumenkranz et al. | |
| 9,901,408 B2 | 2/2018 | Larkin | |
| 9,918,800 B2 | 3/2018 | Itkowitz et al. | |
| 9,943,375 B2 | 4/2018 | Blumenkranz et al. | |
| 9,948,852 B2 | 4/2018 | Lilagan et al. | |
| 9,949,798 B2 | 4/2018 | Weir | |
| 9,949,802 B2 | 4/2018 | Cooper | |
| 9,952,107 B2 | 4/2018 | Blumenkranz et al. | |
| 9,956,044 B2 | 5/2018 | Gomez et al. | |
| 9,980,778 B2 | 5/2018 | Ohline et al. | |
| 10,008,017 B2 | 6/2018 | Itkowitz et al. | |
| 10,028,793 B2 | 7/2018 | Griffiths et al. | |
| 10,033,308 B2 | 7/2018 | Chaghajerdi et al. | |
| 10,034,719 B2 | 7/2018 | Richmond et al. | |
| 10,052,167 B2 | 8/2018 | Au et al. | |
| 10,085,811 B2 | 10/2018 | Weir et al. | |
| 10,092,165 B2 | 10/2018 | Power | |
| 10,092,344 B2 | 10/2018 | Mohr et al. | |
| 10,123,844 B2 | 11/2018 | Nowlin | |
| 10,188,471 B2 | 1/2019 | Brisson | |
| 10,201,390 B2 | 2/2019 | Swarup et al. | |
| 10,213,202 B2 | 2/2019 | Flanagan et al. | |
| 10,258,416 B2 | 4/2019 | Mintz et al. | |
| 10,278,782 B2 | 5/2019 | Jarc et al. | |
| 10,278,783 B2 | 5/2019 | Itkowitz et al. | |
| 10,282,881 B2 | 5/2019 | Itkowitz et al. | |
| 10,335,242 B2 | 7/2019 | Devengenzo et al. | |
| 10,405,934 B2 | 9/2019 | Prisco et al. | |
| 10,433,922 B2 | 10/2019 | Itkowitz et al. | |
| 10,464,219 B2 | 11/2019 | Robinson et al. | |
| 10,485,621 B2 | 11/2019 | Morrissette et al. | |
| 10,500,004 B2 | 12/2019 | Hanuschik et al. | |
| 10,500,005 B2 | 12/2019 | Weir et al. | |
| 10,500,007 B2 | 12/2019 | Richmond et al. | |
| 10,507,066 B2 | 12/2019 | DiMaio et al. | |
| 10,510,267 B2 | 12/2019 | Jarc et al. | |
| 10,524,871 B2 | 1/2020 | Liao | |
| 10,548,459 B2 | 2/2020 | Itkowitz et al. | |
| 10,575,909 B2 | 3/2020 | Robinson et al. | |
| 10,592,529 B2 | 3/2020 | Hoffman et al. | |
| 10,595,946 B2 | 3/2020 | Nixon | |
| 10,881,469 B2 | 1/2021 | Robinson | |
| 10,881,473 B2 | 1/2021 | Itkowitz et al. | |
| 10,898,188 B2 | 1/2021 | Burbank | |
| 10,898,189 B2 | 1/2021 | McDonald | |
| 10,905,506 B2 | 2/2021 | Itkowitz et al. | |
| 10,912,544 B2 | 2/2021 | Brisson et al. | |
| 10,912,619 B2 | 2/2021 | Jarc et al. | |
| 10,918,387 B2 | 2/2021 | Duque et al. | |
| 10,918,449 B2 | 2/2021 | Solomon et al. | |
| 10,932,873 B2 | 3/2021 | Griffiths et al. | |
| 10,932,877 B2 | 3/2021 | Devengenzo et al. | |
| 10,939,969 B2 | 3/2021 | Swarup et al. | |
| 10,939,973 B2 | 3/2021 | DiMaio et al. | |
| 10,952,801 B2 | 3/2021 | Miller et al. | |
| 10,965,933 B2 | 3/2021 | Jarc | |
| 10,966,742 B2 | 4/2021 | Rosa et al. | |
| 10,973,517 B2 | 4/2021 | Wixey | |
| 10,973,519 B2 | 4/2021 | Weir et al. | |
| 10,984,567 B2 | 4/2021 | Itkowitz et al. | |
| 10,993,773 B2 | 5/2021 | Cooper et al. | |
| 10,993,775 B2 | 5/2021 | Cooper et al. | |
| 11,000,331 B2 | 5/2021 | Krom et al. | |

(56) References Cited

U.S. PATENT DOCUMENTS

| | | | |
|---|---|---|---|
| 11,013,567 B2 | 5/2021 | Wu et al. | |
| 11,020,138 B2 | 6/2021 | Ragosta | |
| 11,020,191 B2 | 6/2021 | Diolaiti et al. | |
| 11,020,193 B2 | 6/2021 | Wixey et al. | |
| 11,026,755 B2 | 6/2021 | Weir et al. | |
| 11,026,759 B2 | 6/2021 | Donlon et al. | |
| 11,040,189 B2 | 6/2021 | Vaders et al. | |
| 11,045,077 B2 | 6/2021 | Stern et al. | |
| 11,045,274 B2 | 6/2021 | Dachs et al. | |
| 11,058,501 B2 | 7/2021 | Tokarchuk et al. | |
| 11,076,925 B2 | 8/2021 | DiMaio et al. | |
| 11,090,119 B2 | 8/2021 | Burbank | |
| 11,096,687 B2 | 8/2021 | Flanagan et al. | |
| 11,098,803 B2 | 8/2021 | Duque et al. | |
| 11,109,925 B2 | 9/2021 | Cooper et al. | |
| 11,116,578 B2 | 9/2021 | Hoffman et al. | |
| 11,129,683 B2 | 9/2021 | Steger et al. | |
| 11,135,029 B2 | 10/2021 | Suresh et al. | |
| 11,147,552 B2 | 10/2021 | Burbank et al. | |
| 11,147,640 B2 | 10/2021 | Jarc et al. | |
| 11,154,373 B2 | 10/2021 | Abbott et al. | |
| 11,154,374 B2 | 10/2021 | Hanuschik et al. | |
| 11,160,622 B2 | 11/2021 | Goldberg et al. | |
| 11,160,625 B2 | 11/2021 | Wixey et al. | |
| 11,161,243 B2 | 11/2021 | Rabindran et al. | |
| 11,166,758 B2 | 11/2021 | Mohr et al. | |
| 11,166,770 B2 | 11/2021 | DiMaio et al. | |
| 11,166,773 B2 | 11/2021 | Ragosta et al. | |
| 11,173,597 B2 | 11/2021 | Rabindran et al. | |
| 11,185,378 B2 | 11/2021 | Weir et al. | |
| 11,191,596 B2 | 12/2021 | Thompson et al. | |
| 11,197,729 B2 | 12/2021 | Thompson et al. | |
| 11,213,360 B2 | 1/2022 | Hourtash et al. | |
| 11,221,863 B2 | 1/2022 | Azizian et al. | |
| 11,234,700 B2 | 2/2022 | Ragosta et al. | |
| 11,241,274 B2 | 2/2022 | Vaders et al. | |
| 11,241,290 B2 | 2/2022 | Waterbury et al. | |
| 11,259,870 B2 | 3/2022 | DiMaio et al. | |
| 11,259,884 B2 | 3/2022 | Burbank | |
| 11,272,993 B2 | 3/2022 | Gomez et al. | |
| 11,272,994 B2 | 3/2022 | Saraliev et al. | |
| 11,291,442 B2 | 4/2022 | Wixey et al. | |
| 11,291,513 B2 | 4/2022 | Manzo et al. | |
| 11,376,002 B2 | 7/2022 | Shelton, IV et al. | |
| 11,376,098 B2 | 7/2022 | Shelton, IV et al. | |
| 11,381,759 B2 | 7/2022 | Zhao et al. | |
| 11,382,621 B2 | 7/2022 | Scheib et al. | |
| 11,382,624 B2 | 7/2022 | Harris et al. | |
| 11,382,625 B2 | 7/2022 | Huitema et al. | |
| 11,382,626 B2 | 7/2022 | Shelton, IV et al. | |
| 11,382,627 B2 | 7/2022 | Huitema et al. | |
| 11,382,638 B2 | 7/2022 | Harris et al. | |
| 11,382,644 B2 | 7/2022 | Schoettgen et al. | |
| 11,389,160 B2 | 7/2022 | Shelton, IV et al. | |
| 11,389,255 B2 | 7/2022 | DiMaio et al. | |
| 11,399,906 B2 | 8/2022 | Shelton, IV et al. | |
| 11,406,379 B2 | 8/2022 | Hess et al. | |
| 11,410,259 B2 | 8/2022 | Harris et al. | |
| 11,419,630 B2 | 8/2022 | Yates et al. | |
| 11,424,027 B2 | 8/2022 | Shelton, IV | |
| 11,432,888 B2 | 9/2022 | Diolaiti et al. | |
| 11,432,893 B2 | 9/2022 | Itkowitz et al. | |
| 11,432,895 B2 | 9/2022 | Loh et al. | |
| 11,439,390 B2 | 9/2022 | Patel et al. | |
| 11,439,391 B2 | 9/2022 | Bruns et al. | |
| 11,468,791 B2 | 10/2022 | Jarc et al. | |
| 11,471,155 B2 | 10/2022 | Shelton, IV et al. | |
| 11,471,221 B2 | 10/2022 | Zhao et al. | |
| 11,478,308 B2 | 10/2022 | Hoffman et al. | |
| 11,490,977 B2 | 11/2022 | Schena et al. | |
| 11,497,499 B2 | 11/2022 | Shelton, IV et al. | |
| 11,504,119 B2 | 11/2022 | Shelton, IV et al. | |
| 11,504,124 B2 | 11/2022 | Patel et al. | |
| 11,510,743 B2 | 11/2022 | Shelton, IV et al. | |
| 11,517,312 B2 | 12/2022 | Wixey | |
| 11,517,325 B2 | 12/2022 | Shelton, IV et al. | |
| 11,518,048 B2 | 12/2022 | Saraliev et al. | |
| 2008/0303388 A1* | 12/2008 | Petrovich | A61B 50/10 312/209 |
| 2010/0264738 A1* | 10/2010 | Murtha | G06F 1/263 307/66 |
| 2015/0223890 A1* | 8/2015 | Miller | A61B 50/10 726/17 |
| 2016/0346930 A1* | 12/2016 | Hares | A61B 34/30 |
| 2019/0388137 A1* | 12/2019 | Henrywood | A61B 18/16 |
| 2020/0129250 A1* | 4/2020 | Kapadia | A61B 34/25 |
| 2020/0287392 A1* | 9/2020 | Cooper | H02J 7/0042 |
| 2022/0142723 A1 | 5/2022 | Naclerio | |
| 2022/0203007 A1* | 6/2022 | Yuds | A61M 1/28 |
| 2022/0218432 A1* | 7/2022 | Hannaford | A61B 34/00 |
| 2022/0395338 A1* | 12/2022 | Roberts | A61B 34/30 |
| 2023/0097023 A1* | 3/2023 | Hagn | A61B 90/361 700/247 |
| 2023/0320794 A1* | 10/2023 | Scholan | A61B 34/30 606/1 |
| 2023/0346489 A1* | 11/2023 | Naclerio | B25J 5/007 |

FOREIGN PATENT DOCUMENTS

| | | | | |
|---|---|---|---|---|
| GB | 2601645 A | * | 6/2022 | A61B 90/98 |
| WO | WO-2021158354 A1 | * | 8/2021 | H02J 9/06 |
| WO | WO-2021158383 A1 | * | 8/2021 | A61B 34/30 |
| WO | 2021214454 A1 | | 10/2021 | |
| WO | WO-2020214194 A1 | * | 10/2022 | A61B 50/13 |

* cited by examiner

SURGICAL ROBOTIC SYSTEM AND METHOD FOR CART POWER SWITCHOVER

CROSS-REFERENCE TO RELATED APPLICATIONS

This application claims the benefit of, and priority to, U.S. Provisional Patent Application Ser. No. 63/441,221 filed on Jan. 26, 2023. The entire contents of the foregoing application are incorporated by reference herein.

BACKGROUND

Surgical robotic systems are used in a variety of surgical procedures, including minimally invasive medical procedures. Some surgical robotic systems include a surgeon console controlling a surgical robotic arm and a surgical instrument having an end effector (e.g., forceps or grasping instrument) coupled to and actuated by the robotic arm. In operation, the robotic arm is moved to a position over a patient and then guides the surgical instrument into a small incision via a surgical port or a natural orifice of a patient to position the end effector at a work site within the patient's body. Surgical robotic systems may be used with movable carts supporting one or more arms holding instrument(s). The mobile carts may be coupled to a source of electrical power via a cable. It is desirable to provide backup sources of power for the mobile carts and corresponding switchover circuits.

SUMMARY

According to one embodiment of the present disclosure, a power delivery system for a surgical robotic movable cart is disclosed. The power delivery system includes a power input configured to receive a first DC electrical signal, a first voltage sense and control circuit coupled to the power input and operable in a primary power mode to output the first DC electrical signal, and a battery configured to output a second DC electrical signal. The system also includes a battery charging circuit configured to receive the first DC electrical signal and to charge the battery, and a second voltage sense and control circuit coupled to the battery and operable in a battery power mode to output the second DC electrical signal. The system further includes a sharing circuit configured to output at least one of the first DC electrical signal from the first voltage sense and control circuit or the second DC electrical signal from the second voltage sense and control circuit.

Implementations of the above embodiment may include one or more of the following features. According to one aspect of the above embodiment, the first and second voltage sense and control circuits may be configured to receive a user input to switch between the primary power mode and the battery power mode. The power delivery system includes a cable detection circuit configured to monitor connection of the power input to a cable. The first and second voltage sense and control circuits may be further configured to switch from the primary power mode to the battery power mode in response to detection of a cable disconnection. The second voltage sense and control circuit may be also configured to monitor a state of charge of the battery and to enable a switch from the primary power mode to the battery power mode in response to the state of charge being above a state of charge threshold.

According to another embodiment of the present disclosure, a surgical robotic system is disclosed. The surgical robotic system includes a control tower having a DC power source and a movable cart supporting a robotic arm having at least one of a camera or an instrument. The movable cart includes a power delivery system having a power input configured to receive a first DC electrical signal from the DC power source, a first voltage sense and control circuit coupled to the power input and operable in a primary power mode to output the first DC electrical signal, and a battery configured to output a second DC electrical signal. The power delivery system of the movable cart further includes a battery charging circuit configured to receive the first DC electrical signal and to charge the battery, and a second voltage sense and control circuit coupled to the battery and operable in a battery power mode to output the second DC electrical signal. The power delivery system of the movable cart further includes a sharing circuit configured to output at least one of the first DC electrical signal from the first voltage sense and control circuit or the second DC electrical signal from the second voltage sense and control circuit to power the movable cart.

Implementations of the above embodiment may include one or more of the following features. According to one aspect of the above embodiment, the first and second voltage sense and control circuits may be configured to receive a user input to switch between the primary power mode and the battery power mode. The surgical robotic system may further include a display configured to output a graphical user interface for receiving the user input. The surgical robotic system additionally includes a cable detection circuit configured to monitor connection of the power input to a cable. The first and second voltage sense and control circuits may be also configured to switch from the primary power mode to the battery power mode in response to detection of a cable disconnection. The cable detection circuit also includes a detection signal source disposed at the control tower, the detection signal source configured to generate a detection signal. The cable detection circuit further includes a first cable monitor disposed at the movable cart, the first cable monitor configured to monitor the detection signal. The cable detection circuit may further include a second cable monitor disposed at the control tower, the second cable monitor configured to monitor the detection signal returned from the movable cart. The cable detection circuit may be also configured to determine cable disconnection based on at least one of the first cable monitor or the second cable monitor failing to receive the detection signal. The second voltage sense and control circuit may be further configured to monitor a state of charge of the battery and to enable a switch from the primary power mode to the battery power mode in response to the state of charge being above a state of charge threshold.

According to a further embodiment of the present disclosure, a method for controlling power delivery to a surgical robotic movable cart is disclosed. The method includes supplying a first DC electrical signal from a DC power source housed in a control tower to a power input of a movable cart and outputting the first DC electrical signal through a first voltage sense and control circuit operable in a primary power mode. The method also includes receiving the first DC electrical signal at a battery charging circuit, charging a battery using the first DC electrical signal, and supplying a second DC electrical signal from the battery. The method further includes outputting the second DC electrical signal through a second voltage sense and control circuit operable in a battery power mode, and outputting through a sharing circuit at least one of the first DC electrical signal from the first voltage sense and control circuit or the second DC electrical signal from the second voltage sense and control circuit to power the movable cart.

Implementations of the above embodiment may include one or more of the following features. According to one aspect of the above embodiment, the method may also include receiving a user input at the first and second voltage sense and control circuits to switch between the primary power mode and the battery power mode. Receiving the user input may be performed through a graphical user interface output on a display. The method may further include monitoring a state of charge of the battery and enabling a switch from the primary power mode to the battery power mode in response to the state of charge being above a state of charge threshold. The method may additionally include monitoring a connection of the power input to a cable at a cable detection circuit and switching from the primary power mode to the battery power mode in response to detection of a cable disconnection. The method may also include generating a detection signal at a detection signal source disposed at the control tower. The method may further include monitoring the detection signal at a first cable monitor disposed at the movable cart and monitoring the detection signal returned from the movable cart at a second cable monitor disposed at the control tower. The method may additionally include determining, at the cable detection circuit, cable disconnection based on at least one of the first cable monitor or the second cable monitor failing to receive the detection signal.

BRIEF DESCRIPTION OF THE DRAWINGS

Various embodiments of the present disclosure are described herein with reference to the drawings wherein.

DETAILED DESCRIPTION

Figure 1:
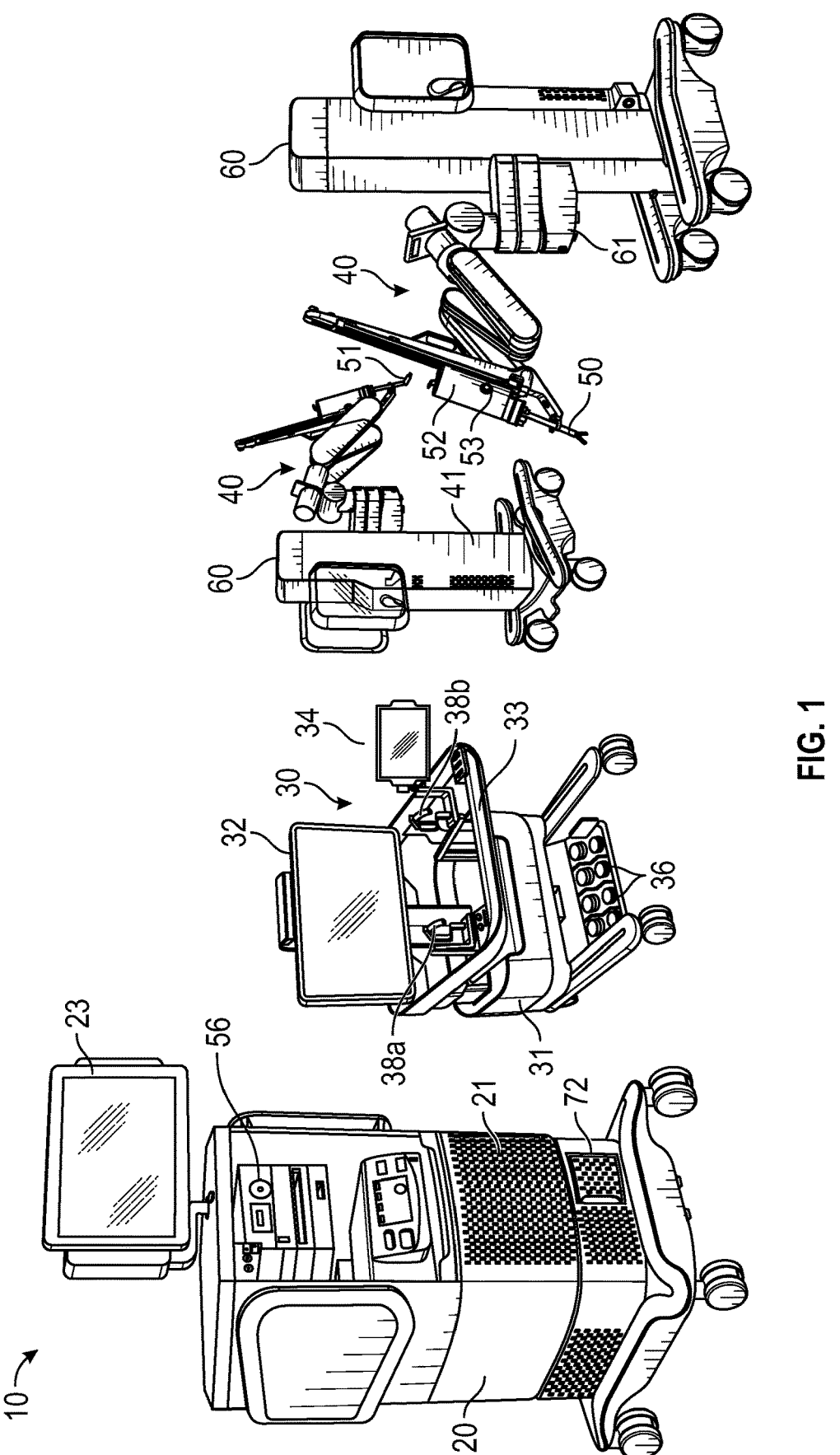
FIG. 1 is a schematic illustration of a surgical robotic system including a control tower, a console, and one or more surgical robotic arms each disposed on a movable cart according to an embodiment of the present disclosure.

Embodiments of the presently disclosed surgical robotic system are described in detail with reference to the drawings, in which like reference numerals designate identical or corresponding elements in each of the several views.

As will be described in detail below, the present disclosure is directed to a surgical robotic system, which includes a surgeon console, a control tower, and one or more movable carts having a surgical robotic arm coupled to a setup arm. The surgeon console receives user input through one or more interface devices. The input is processed by the control tower as movement commands for moving the surgical robotic arm and an instrument and/or camera coupled thereto. Thus, the surgeon console enables teleoperation of the surgical arms and attached instruments/camera. The surgical robotic arm includes a controller, which is configured to process the movement commands to control one or more actuators of the robotic arm, which would, in turn, move the robotic arm and the instrument in response to the movement commands.

With reference to FIG. 1, a surgical robotic system 10 includes a control tower 20, which is connected to all of the components of the surgical robotic system 10 including a surgeon console 30 and one or more movable carts 60. Each of the movable carts 60 includes a robotic arm 40 having a surgical instrument 50 coupled thereto. The robotic arms 40 also couple to the movable carts 60. The robotic system 10 may include any number of movable carts 60 and/or robotic arms 40.

The surgical instrument 50 is configured for use during minimally invasive surgical procedures. In embodiments, the surgical instrument 50 may be configured for open surgical procedures. In further embodiments, the surgical instrument 50 may be an electrosurgical forceps configured to seal tissue by compressing tissue between jaw members and applying electrosurgical current thereto. In yet further embodiments, the surgical instrument 50 may be a surgical stapler including a pair of jaws configured to grasp and clamp tissue while deploying a plurality of tissue fasteners, e.g., staples, and cutting stapled tissue. In yet further embodiments, the surgical instrument 50 may be a surgical clip applier including a pair of jaws configured apply a surgical clip onto tissue.

One of the robotic arms 40 may include an endoscopic camera 51 configured to capture video of the surgical site. The endoscopic camera 51 may be a stereoscopic endoscope configured to capture two side-by-side (i.e., left and right) images of the surgical site to produce a video stream of the surgical scene. The endoscopic camera 51 is coupled to a video processing device 56, which may be disposed within the control tower 20. The video processing device 56 may be any computing device as described below configured to receive the video feed from the endoscopic camera 51 and output the processed video stream.

The surgeon console 30 includes a first display 32, which displays a video feed of the surgical site provided by camera 51 disposed on the robotic arm 40, and a second display 34, which displays a user interface for controlling the surgical robotic system 10. The first display 32 and second display 34 may be touchscreens allowing for displaying various graphical user inputs.

The surgeon console 30 also includes a plurality of user interface devices, such as foot pedals 36 and a pair of handle controllers 38a and 38b which are used by a user to remotely control robotic arms 40. The surgeon console further includes an armrest 33 used to support clinician's arms while operating the handle controllers 38a and 38b.

The control tower 20 includes a display 23, which may be a touchscreen, and outputs on the graphical user interfaces (GUIs). The control tower 20 also acts as an interface between the surgeon console 30 and one or more robotic arms 40. In particular, the control tower 20 is configured to control the robotic arms 40, such as to move the robotic arms 40 and the corresponding surgical instrument 50, based on a set of programmable instructions and/or input commands from the surgeon console 30, in such a way that robotic arms 40 and the surgical instrument 50 execute a desired movement sequence in response to input from the foot pedals 36 and the handle controllers 38a and 38b. The foot pedals 36 may be used to enable and lock the hand controllers 38a and 38b, repositioning camera movement and electrosurgical activation/deactivation. In particular, the foot pedals 36 may be used to perform a clutching action on the hand controllers 38a and 38b. Clutching is initiated by pressing one of the foot pedals 36, which disconnects (i.e., prevents movement inputs) the hand controllers 38a and/or 38b from the robotic arm 40 and corresponding instrument 50 or camera 51 attached thereto. This allows the user to reposition the hand controllers 38a and 38b without moving the robotic arm(s) 40 and the instrument 50 and/or camera 51. This is useful when reaching control boundaries of the surgical space.

Each of the control tower 20, the surgeon console 30, and the robotic arm 40 includes a respective computer 21, 31, 41. The computers 21, 31, 41 are interconnected to each other using any suitable communication network based on wired or wireless communication protocols. The term "network," whether plural or singular, as used herein, denotes a data network, including, but not limited to, the Internet, Intranet, a wide area network, or a local area network, and without limitation as to the full scope of the definition of communication networks as encompassed by the present disclosure. Suitable protocols include, but are not limited to, transmission control protocol/internet protocol (TCP/IP), datagram protocol/internet protocol (UDP/IP), and/or datagram congestion control protocol (DCCP).

The computers 21, 31, 41 may include any suitable processor (not shown) operably connected to a memory (not shown), which may include one or more of volatile, nonvolatile, magnetic, optical, or electrical media, such as read-only memory (ROM), random access memory (RAM), electrically erasable programmable ROM (EEPROM), nonvolatile RAM (NVRAM), or flash memory. The processor may be any suitable processor (e.g., control circuit) adapted to perform the operations, calculations, and/or set of instructions described in the present disclosure including, but not limited to, a hardware processor, a field programmable gate array (FPGA), a digital signal processor (DSP), a central processing unit (CPU), a microprocessor, and combinations thereof. Those skilled in the art will appreciate that the processor may be substituted for by using any logic processor (e.g., control circuit) adapted to execute algorithms, calculations, and/or set of instructions described herein.

Figure 2:
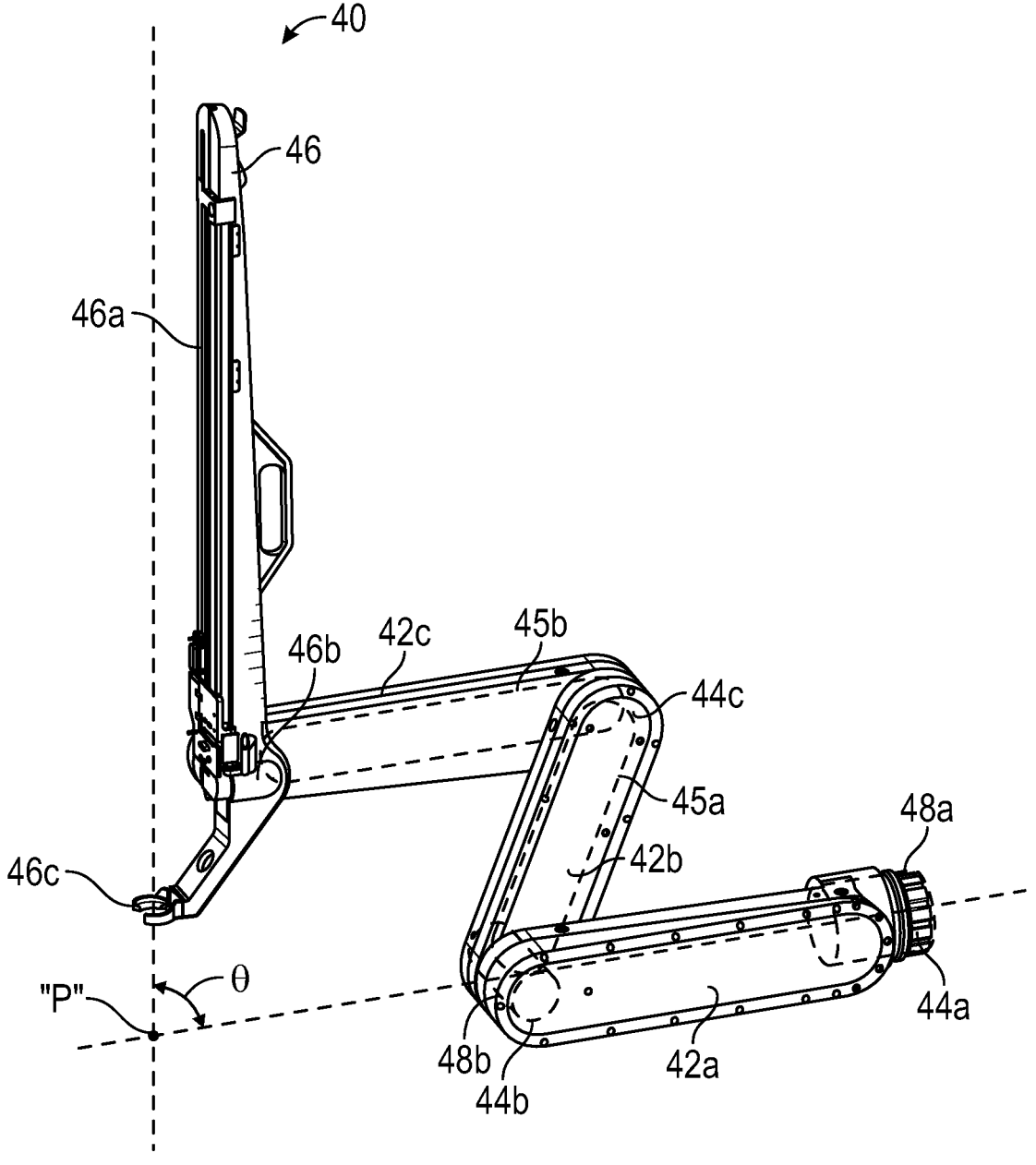
FIG. 2 is a perspective view of a surgical robotic arm of the surgical robotic system of FIG. 1 according to an embodiment of the present disclosure.
Figure 3:
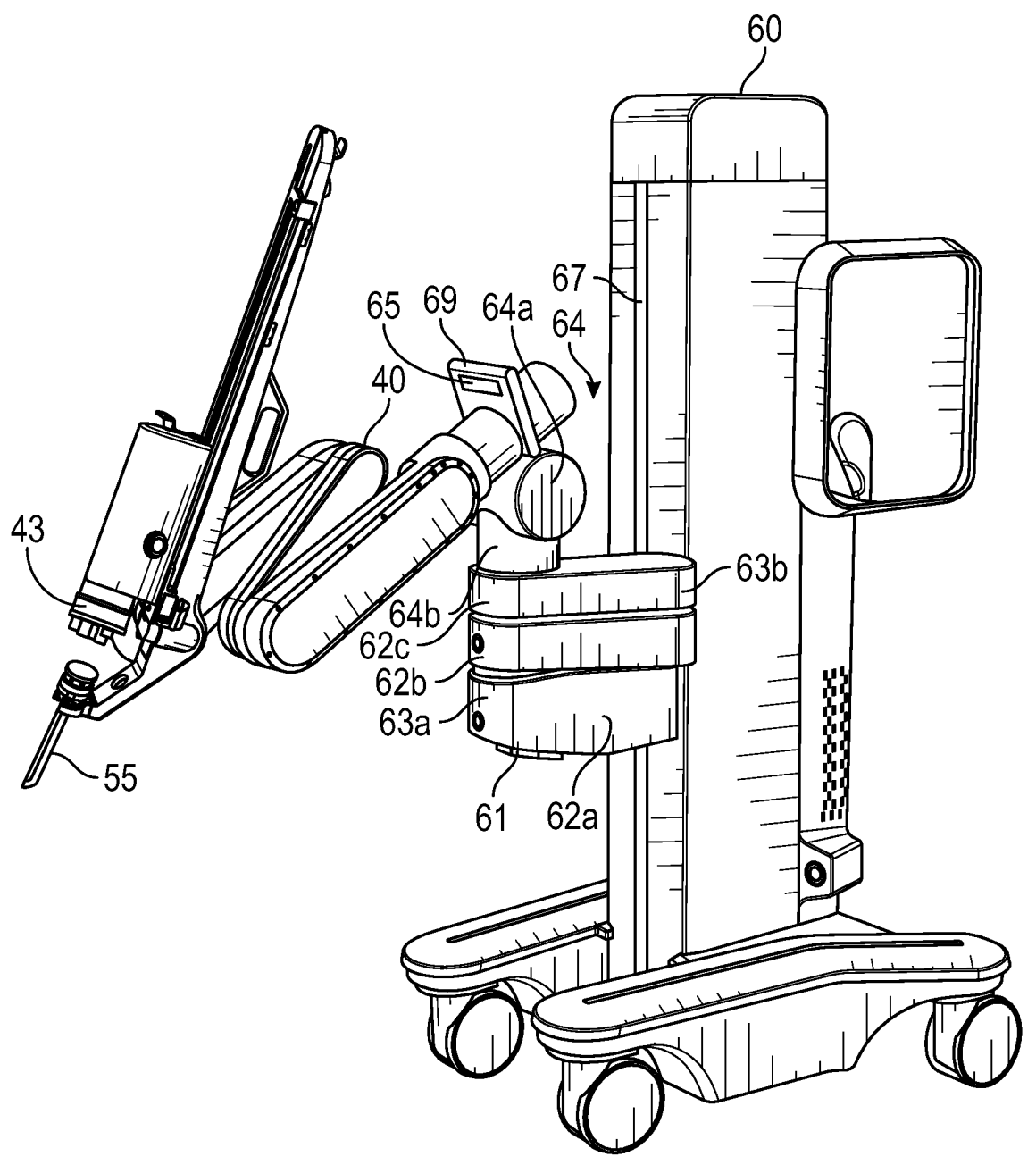
FIG. 3 is a perspective view of a movable cart having a setup arm with the surgical robotic arm of the surgical robotic system of FIG. 1 according to an embodiment of the present disclosure.

With reference to FIG. 2, each of the robotic arms 40 may include a plurality of links 42a, 42b, 42c, which are interconnected at joints 44a, 44b, 44c, respectively. Other configurations of links and joints may be utilized as known by those skilled in the art. The joint 44a is configured to secure the robotic arm 40 to the movable cart 60 and defines a first longitudinal axis. With reference to FIG. 3, the movable cart 60 includes a lift 67 and a setup arm 61, which provides a base for mounting of the robotic arm 40. The lift 67 allows for vertical movement of the setup arm 61. The movable cart 60 also includes a display 69 for displaying information pertaining to the robotic arm 40. In embodiments, the robotic arm 40 may include any type and/or number of joints.

The setup arm 61 includes a first link 62a, a second link 62b, and a third link 62c, which provide for lateral maneuverability of the robotic arm 40. The links 62a, 62b, 62c are interconnected at joints 63a and 63b, each of which may include an actuator (not shown) for rotating the links 62b and 62b relative to each other and the link 62c. In particular, the links 62a, 62b, 62c are movable in their corresponding lateral planes that are parallel to each other, thereby allowing for extension of the robotic arm 40 relative to the patient (e.g., surgical table). In embodiments, the robotic arm 40 may be coupled to the surgical table (not shown). The setup arm 61 includes controls 65 for adjusting movement of the links 62a, 62b, 62c as well as the lift 67. In embodiments, the setup arm 61 may include any type and/or number of joints.

The third link 62c may include a rotatable base 64 having two degrees of freedom. In particular, the rotatable base 64 includes a first actuator 64a and a second actuator 64b. The first actuator 64a is rotatable about a first stationary arm axis which is perpendicular to a plane defined by the third link 62c and the second actuator 64b is rotatable about a second stationary arm axis which is transverse to the first stationary arm axis. The first and second actuators 64a and 64b allow for full three-dimensional orientation of the robotic arm 40.

The actuator 48b of the joint 44b is coupled to the joint 44c via the belt 45a, and the joint 44c is in turn coupled to the joint 46b via the belt 45b. Joint 44c may include a transfer case coupling the belts 45a and 45b, such that the actuator 48b is configured to rotate each of the links 42b, 42c and a holder 46 relative to each other. More specifically, links 42b, 42c, and the holder 46 are passively coupled to the actuator 48b which enforces rotation about a pivot point "P" which lies at an intersection of the first axis defined by the link 42a and the second axis defined by the holder 46. In other words, the pivot point "P" is a remote center of motion (RCM) for the robotic arm 40. Thus, the actuator 48b controls the angle θ between the first and second axes allowing for orientation of the surgical instrument 50. Due to the interlinking of the links 42a, 42b, 42c, and the holder 46 via the belts 45a and 45b, the angles between the links 42a, 42b, 42c, and the holder 46 are also adjusted in order to achieve the desired angle θ. In embodiments, some or all of the joints 44a, 44b, 44c may include an actuator to obviate the need for mechanical linkages.

The joints 44a and 44b include an actuator 48a and 48b configured to drive the joints 44a, 44b, 44c relative to each other through a series of belts 45a and 45b or other mechanical linkages such as a drive rod, a cable, or a lever and the like. In particular, the actuator 48a is configured to rotate the robotic arm 40 about a longitudinal axis defined by the link 42a.

With reference to FIG. 2, the holder 46 defines a second longitudinal axis and is configured to receive an instrument drive unit (IDU) 52 (FIG. 1). The IDU 52 is configured to couple to an actuation mechanism of the surgical instrument 50 and/or the camera 51 and is configured to move (e.g., rotate) and actuate the instrument 50 and/or the camera 51. IDU 52 transfers actuation forces from its actuators to the surgical instrument 50. The holder 46 includes a sliding mechanism 46a, which is configured to move the IDU 52 along the second longitudinal axis defined by the holder 46. The holder 46 also includes a joint 46b, which rotates the holder 46 relative to the link 42c. During endoscopic procedures, the instrument 50 may be inserted through an endoscopic access port 55 (FIG. 3) held by the holder 46. The holder 46 also includes a port latch 46c for securing the access port 55 to the holder 46 (FIG. 2).

The IDU 52 is attached to the holder 46, followed by a sterile interface module (SIM) 43 being attached to a distal portion of the IDU 52. The SIM 43 is configured to secure a sterile drape (not shown) to the IDU 52. The instrument 50 is then attached to the SIM 43. The instrument 50 is then inserted through the access port 55 by moving the IDU 52 along the holder 46. The SIM 43 includes a plurality of drive shafts configured to transmit rotation of individual motors of the IDU 52 to the instrument 50 thereby actuating the instrument 50. In addition, the SIM 43 provides a sterile barrier between the instrument 50 and the other components of robotic arm 40, including the IDU 52.

The robotic arm 40 also includes a plurality of manual override buttons 53 (FIG. 1) disposed on the IDU 52 and the setup arm 61, which may be used in a manual mode. The user may press one or more of the buttons 53 to move the component associated with the button 53.

Figure 4:
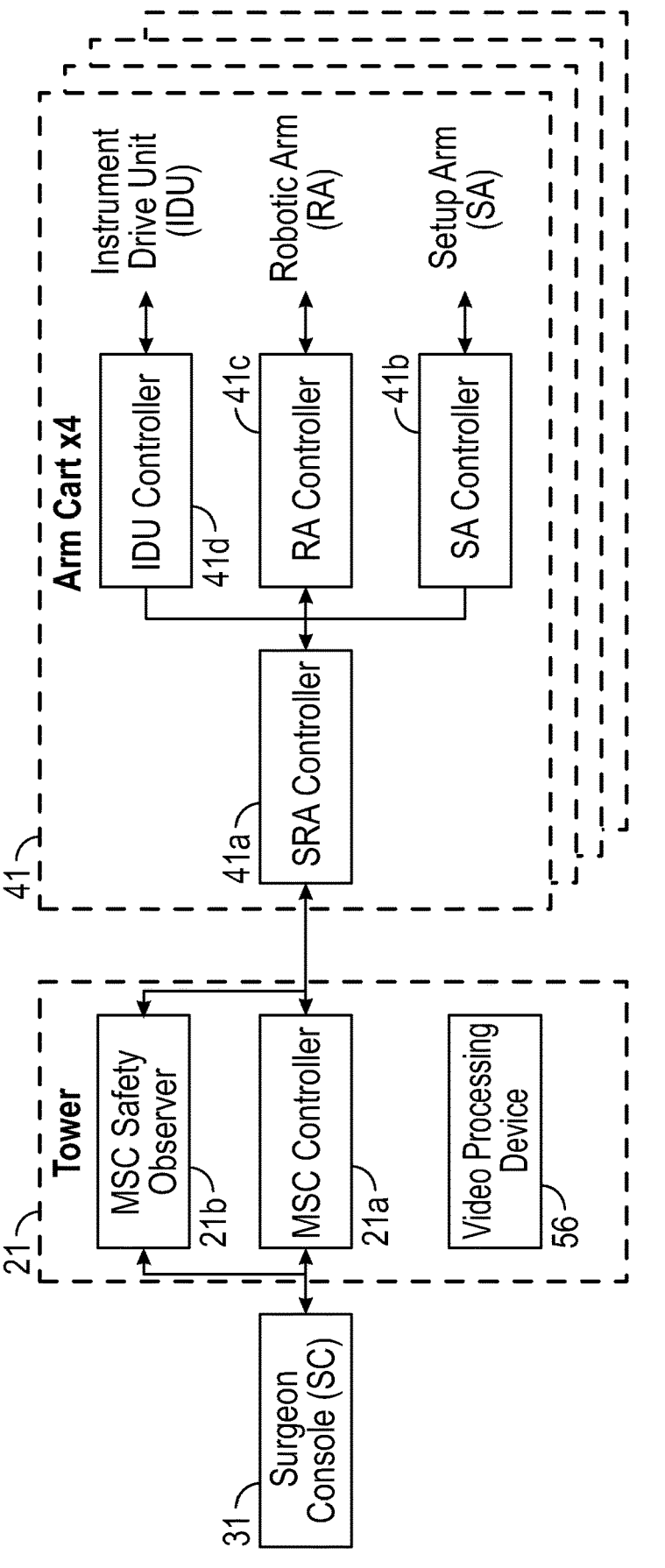
FIG. 4 is a schematic diagram of a computer architecture of the surgical robotic system of FIG. 1 according to an embodiment of the present disclosure.

With reference to FIG. 4, each of the computers 21, 31, 41 of the surgical robotic system 10 may include a plurality of controllers, which may be embodied in hardware and/or software. The computer 21 of the control tower 20 includes a controller 21a and safety observer 21b. The controller 21a receives data from the computer 31 of the surgeon console 30 about the current position and/or orientation of the handle controllers 38a and 38b and the state of the foot pedals 36 and other buttons. The controller 21a processes these input positions to determine desired drive commands for each joint of the robotic arm 40 and/or the IDU 52 and communicates these to the computer 41 of the robotic arm 40. The controller 21a also receives the actual joint angles measured by encoders of the actuators 48a and 48b and uses this information to determine force feedback commands that are transmitted back to the computer 31 of the surgeon console 30 to provide haptic feedback through the handle controllers 38a and 38b. The safety observer 21b performs validity checks on the data going into and out of the controller 21a and notifies a system fault handler if errors in the data transmission are detected to place the computer 21 and/or the surgical robotic system 10 into a safe state.

The computer 41 includes a plurality of controllers, namely, a main cart controller 41a, a setup arm controller 41b, a robotic arm controller 41c, and an instrument drive unit (IDU) controller 41d. The main cart controller 41a receives and processes joint commands from the controller 21a of the computer 21 and communicates them to the setup arm controller 41b, the robotic arm controller 41c, and the IDU controller 41d. The main cart controller 41a also manages instrument exchanges and the overall state of the movable cart 60, the robotic arm 40, and the IDU 52. The main cart controller 41a also communicates actual joint angles back to the controller 21a.

Each of joints 63a and 63b and the rotatable base 64 of the setup arm 61 are passive joints (i.e., no actuators are present therein) allowing for manual adjustment thereof by a user. The joints 63a and 63b and the rotatable base 64 include brakes that are disengaged by the user to configure the setup arm 61. The setup arm controller 41b monitors slippage of each of joints 63a and 63b and the rotatable base 64 of the setup arm 61, when brakes are engaged or can be freely moved by the operator when brakes are disengaged, but do not impact controls of other joints. The robotic arm controller 41c controls each joint 44a and 44b of the robotic arm 40 and calculates desired motor torques required for gravity compensation, friction compensation, and closed loop position control of the robotic arm 40. The robotic arm controller 41c calculates a movement command based on the calculated torque. The calculated motor commands are then communicated to one or more of the actuators 48a and 48b in the robotic arm 40. The actual joint positions are then transmitted by the actuators 48a and 48b back to the robotic arm controller 41c.

The IDU controller 41d receives desired joint angles for the surgical instrument 50, such as wrist and jaw angles, and computes desired currents for the motors in the IDU 52. The IDU controller 41d calculates actual angles based on the motor positions and transmits the actual angles back to the main cart controller 41a.

The robotic arm 40 is controlled in response to a pose of the handle controller controlling the robotic arm 40, e.g., the handle controller 38a, which is transformed into a desired pose of the robotic arm 40 through a hand eye transform function executed by the controller 21a. The hand eye function, as well as other functions described herein, is/are embodied in software executable by the controller 21a or any other suitable controller described herein. The pose of one of the handle controllers 38a may be embodied as a coordinate position and roll-pitch-yaw (RPY) orientation relative to a coordinate reference frame, which is fixed to the surgeon console 30. The desired pose of the instrument 50 is relative to a fixed frame on the robotic arm 40. The pose of the handle controller 38a is then scaled by a scaling function executed by the controller 21a. In embodiments, the coordinate position may be scaled down and the orientation may be scaled up by the scaling function. In addition, the controller 21a may also execute a clutching function, which disengages the handle controller 38a from the robotic arm 40. In particular, the controller 21a stops transmitting movement commands from the handle controller 38a to the robotic arm 40 if certain movement limits or other thresholds are exceeded and in essence acts like a virtual clutch mechanism, e.g., limits mechanical input from effecting mechanical output.

The desired pose of the robotic arm 40 is based on the pose of the handle controller 38a and is then passed by an inverse kinematics function executed by the controller 21a. The inverse kinematics function calculates angles for the joints 44a, 44b, 44c of the robotic arm 40 that achieve the scaled and adjusted pose input by the handle controller 38a. The calculated angles are then passed to the robotic arm controller 41c, which includes a joint axis controller having a proportional-derivative (PD) controller, the friction estimator module, the gravity compensator module, and a two-sided saturation block, which is configured to limit the commanded torque of the motors of the joints 44a, 44b, 44c.

Figure 5:
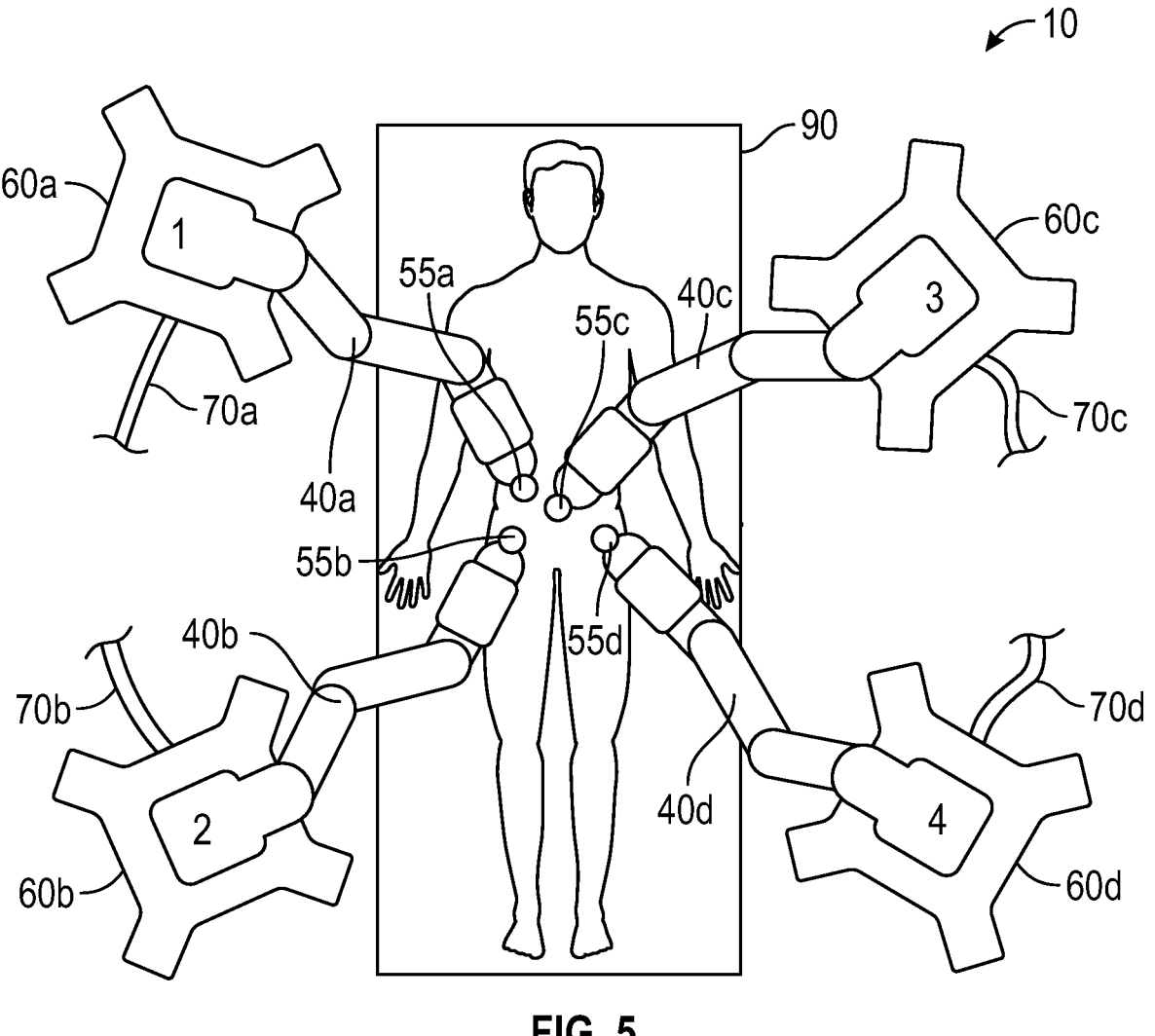
FIG. 5 is a plan schematic view of movable carts of FIG. 1 positioned about a surgical table according to an embodiment of the present disclosure.

With reference to FIG. 5, the surgical robotic system 10 is setup around a surgical table 90. The system 10 includes movable carts 60a-d, which may be numbered "1" through "4." During setup, each of the carts 60a-d is positioned around the surgical table 90. Position and orientation of the carts 60a-d depends on a plurality of factors, such as placement of a plurality of access ports 55a-d, which in turn, depends on the surgery being performed. Once the port placements are determined, the access ports 55a-d are inserted into the patient, and carts 60a-d are positioned to insert instruments 50 and the endoscopic camera 51 into corresponding ports 55a-d. During use, each of the robotic arms 40a-d is attached to one of the access ports 55a-d that is inserted into the patient by attaching the latch 46c (FIG. 2) to the access port 55 (FIG. 3). The IDU 52 is attached to the holder 46, followed by the SIM 43 being attached to a distal portion of the IDU 52. Thereafter, the instrument 50 is attached to the SIM 43. The instrument 50 is then calibrated by the robotic arm 40 and is inserted through the access port 55 by moving the IDU 52 along the holder 46.

The carts 60a-d are connected to the control tower 20 via hybrid cables 70a-d, respectively, which transmit data communication and electrical power between the control tower 20 and the carts 60a-d. In addition to acting a central communication and control hub, the control tower 20 also distributes and manages electrical power to the carts 60a-d. The control tower 20 is coupled to an electrical power source, e.g., 120 VAC standard line voltage, and also includes a backup power source 72 (FIG. 1), e.g., one or more batteries, that provide uninterrupted supply of power in the event of disconnection of electrical power to the control tower 20. Thus, in the event of an interruption of electrical power, the control tower 20 also powers the carts 60a-d. The control tower 20 provides a DC voltage, e.g., +48V to each of the four carts 60a-d though four cables 70a-d.

It is difficult to reposition the carts 60a-d in the operating room while the carts 60a-d are connected to the control tower 20. Movement of the carts 60a-d may be hindered due to the sheer size of the carts 60a-d and the lack of flexibility and lengths of the four hybrid cables 70a-d. Once the carts 60a-d are situated, power has been applied, and the calibration process has concluded, removing one of the cables 70a-d from any of the carts 60a-d in order to reposition the carts is further complicated. Losing power results in the cart rebooting and requires redoing of the calibration process, further delaying the start of the surgical procedure. The present disclosure provides for a system and method enabling disconnection of fully calibrated cart 60a from the cable 70a for a short period of time to be able to reposition the cart 60a without being hindered by the umbilical connection and without spending the time on rebooting and recalibration.

Figures 6, 7:
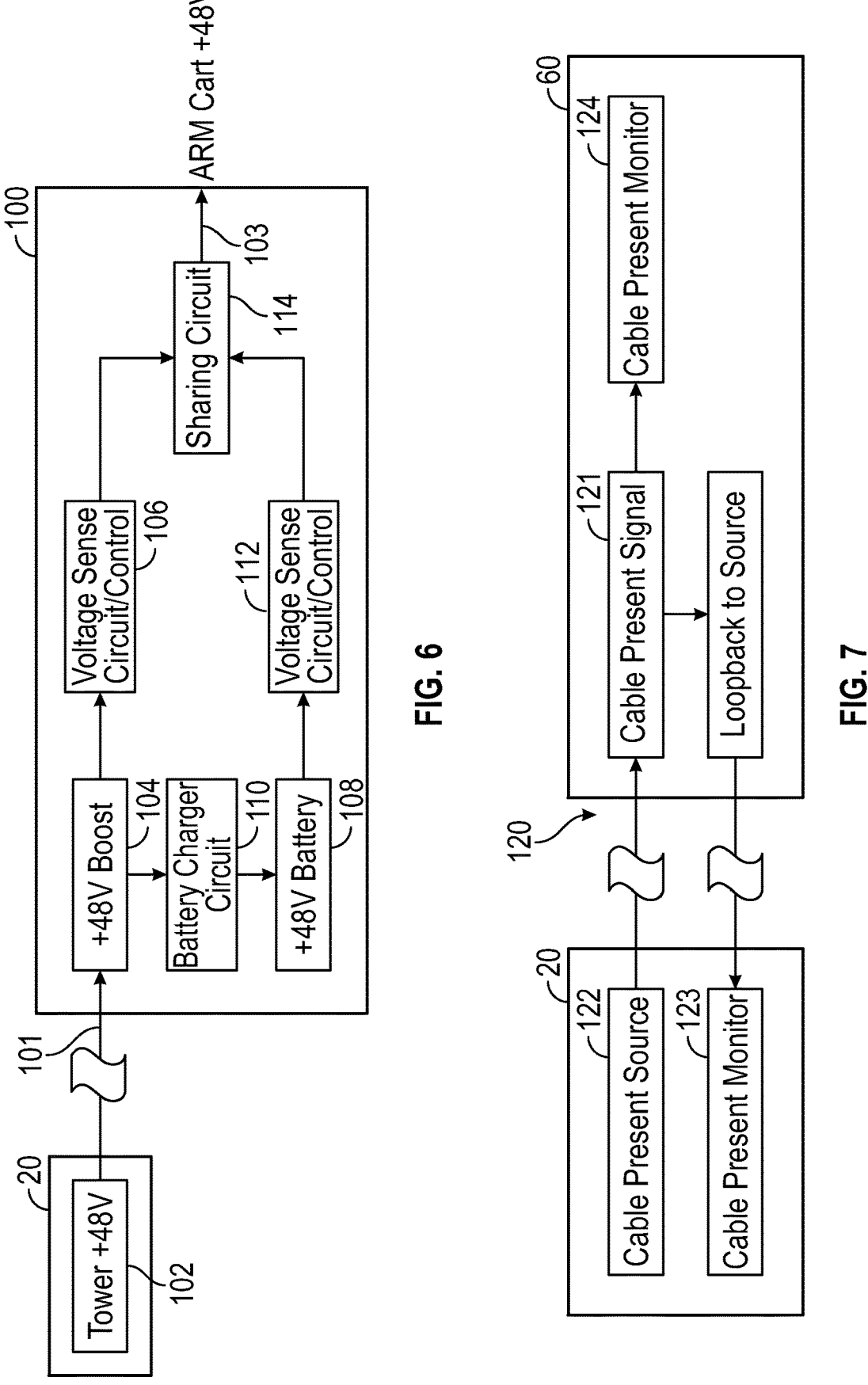
FIG. 6 is a schematic diagram of a movable cart power architecture according to an embodiment of the present disclosure.
FIG. 7 is a schematic diagram of a cable detection circuit according to an embodiment of the present disclosure.

FIG. 6 shows a power delivery system 100 configured to independently power any one of the carts 60a-d during robotic arm setup to bridge the time, e.g., about five minutes, between one of the cables 70a-d being removed for repositioning of any one of the carts 60a-d and reconnection of the removed cable of cables 70a-d. The components of the power delivery system 100 may be disposed on or within the carts 60a-d. The carts 60a-d include a battery 108 configured to power the carts 60a-d in the event the cables 70a-d are disconnected. The battery 108 is configured to deliver DC voltage at the same voltage as the control tower 20. The duration of the power supply of the battery 108 may be expanded via increased battery capacity, to provide backup power during for longer power interruptions, e.g., during the procedure to perform emergency movement of the robotic arms 40a-d and to extract the instruments 50.

The control tower 20 provides power to each of the four carts 60a-d though four cables 70a-d using a tower power supply controller (TPSC) 102 at a voltage input 101. Transmission through the cables 70a-d cause a voltage drop proportional to the resistance and DC current draw of the carts 60a-d. To compensate for the voltage drop, the system 100 includes a voltage booster circuit 104 disposed in the carts 60a-d to boost the lowered DC voltage to the DC voltage output by the TPSC 102, e.g., +48V. This boosted DC voltage is used to power the carts 60a-d and to charge the battery 108.

The power delivery system 100 also includes a first voltage sense and control circuit 106, which includes a voltage sensor, overvoltage protection circuit, and a processor (e.g., FPGA) configured to perform a variety of functions, including: verifying that the DC voltage is at the correct level, protecting the DC voltage boost circuit and control tower 20 DC voltage power supply from any back electromagnetic fields (EMF) created by the motors in the carts 60a-d, verifying that the current limit of the cart 60a is not exceeded, and providing software control for a controlled switchover between voltage provided by the control tower 20 and voltage provided by the battery 108 of the carts 70a-d. A controlled switchover is defined as the condition when the user has decided to unplug one of the cables 70a-d but wants to keep the carts 60a-d powered. The action may be initiated by the user via a GUI and under automatic software control. The GUI may be displayed on any of the displays 23, 32, 34 of the system 10 or the controls 65 of the carts 60a-d (FIG. 3). In embodiments, switchover may be automatically initiated by unplugging one or more of the cables 70a-d. The first voltage sense and control circuit 106 is configured to automatically switch over from voltage supplied by the TPSC 102 to the battery 108 by detecting an interruption (e.g., drop to 0V) in the voltage supplied by the TPSC 102 and/or disconnection of the cables 70a-d.

The carts 60a-d also include a battery charger circuit 110, which is used to maintain the battery 108 fully charged by checking the state of charge of the battery 108 and to charge the battery 108 when appropriate. The battery charger circuit 110 includes one or more sensors (e.g., current and voltage sensors) and a processor configured to execute a suitable smart battery charge algorithm to maintain the overall health of the battery 108. The processor of the battery charger circuit 110 may also include a fuel gauge algorithm so that the main cart controller 41a of the carts 70a-d can monitor the state of charge of the battery 108. The state of charge may be used as a parameter to prevent switchover from being commenced if the battery capacity is below a preset level that would be required to provide enough power to the cart 60a to last the allotted time.

The carts 60a-d further include a second voltage sense and control circuit 112, which includes a voltage sensor, overvoltage protection circuit, and a processor (e.g., FPGA) configured to perform a variety of functions, including: verifying that the DC voltage output by the battery 108 is at the correct level, verifying that the current limit of the cart 60a in not exceeded, e.g., due to circuit failure in the carts 60a-d, and providing software control for a controlled switchover between voltage provided by the control tower 20 and the battery 108 of the carts 70a-d. A sharing circuit 114 performs switching between the DC voltage supplied by the control tower 20 DC voltage and DC voltage supplied by the battery 108 allowing the selected source of power to deliver power to the cart 60a through a power output 103.

The first and second voltage sense and control circuits 106 and 112 may be also controlled by a controller (e.g., main controller 21a, main cart controller 41a, etc.) based on user inputs and/or sensor feedback, e.g., from a cable detection circuit 120. FIG. 7 shows the cable detection circuit 120 of the carts 70a-d, which provides the control tower 20 and carts 60a-d with an indication when the cable of cables 70a-d is engaged at both ends, i.e., at the control tower 20 and at one of the carts 60a-d. A uniquely identifiable communication cable present signal 121 is generated at the control tower 20, i.e., cable present source 122, and transmitted to each cart 60a-d. The cart 60a loops back the communication to the control tower 20 so that the control tower 20 can determine the presence of the corresponding cable. Each of the control tower 20 and the carts 60a-d includes a cable present monitor 123 and 124, which confirm that the cables 70a-d are present based on receipt of the looped back signal 121 or the original signal 121, respectively. In particular, the signal 121 is looped back from the cable present source 122 to the cable present monitor 123 of the control tower 20 and also to the cable present monitor 124 of the cart 60.

Thus, the control tower 20 and the carts 60*a-d* use the signal 121 to determine the connection of the cables 70*a-d* to the control tower 20 and to determine that the cables 70*a-d* are present. The lack of the communication signal 121 during the switchover process indicates to the first and second voltage sense and control circuit 106 and 112 when one of the cables 70*a-d* has been disconnected. In this way, both control tower 20 and corresponding cart are notified when the cable has been removed prior to the switchover to battery power mode.

Figure 8:
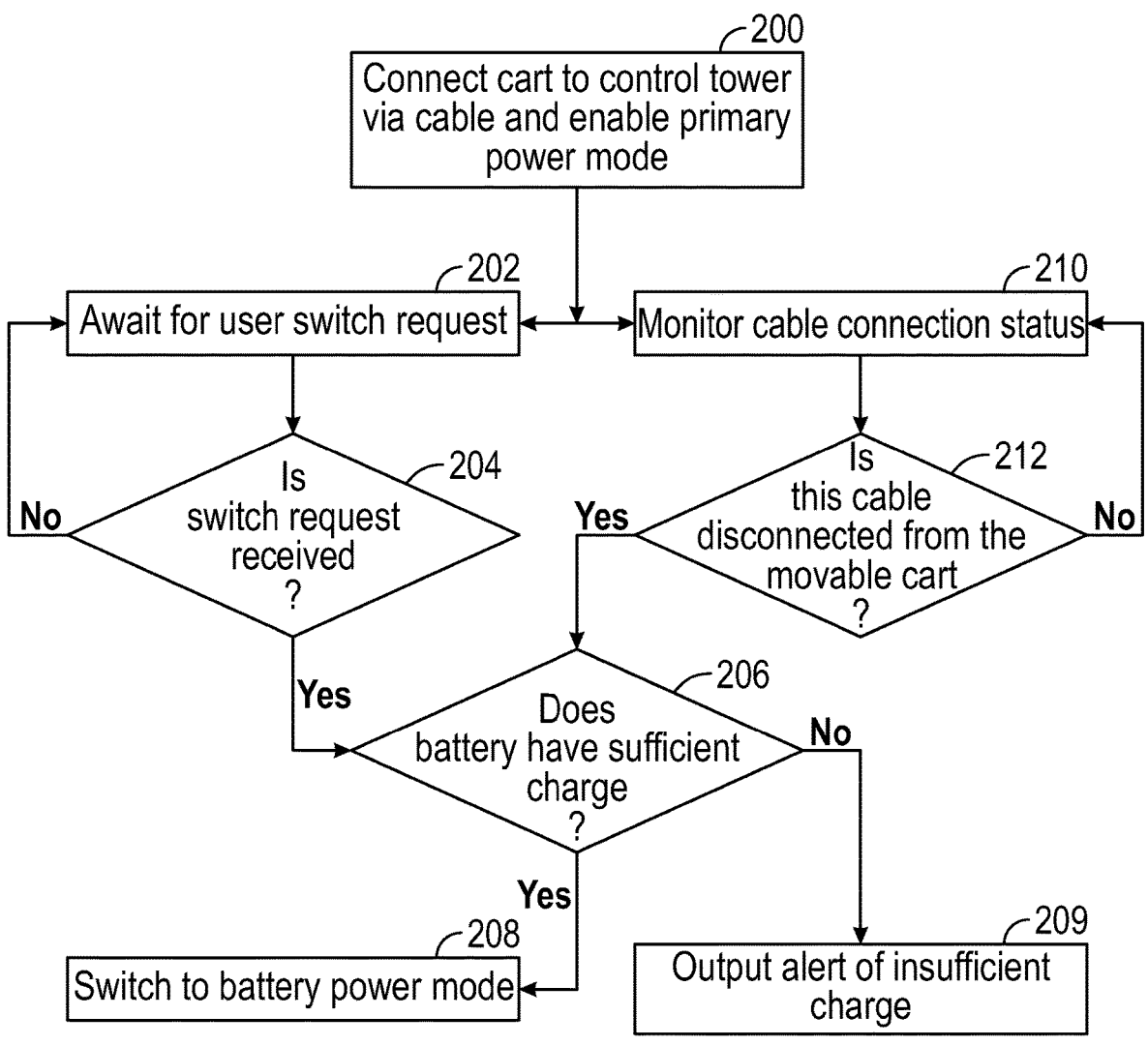
FIG. 8 is a flowchart of a method for switching between power modes for movable carts according to an embodiment of the present disclosure.

With reference to FIG. 8, a method is provided for controlling switchover between a primary power mode, in which the control tower 20 powers the carts 60*a-d* and a battery power mode. The method may be embodied as software instructions executable by any one or more of the controllers of robotic system 10 (e.g., main controller 21*a,* the IDU controller 41*d,* etc.).

Initially, at step 200, the carts 60*a-d* are connected to the control tower 20 via the cables 70*a-d*. The robotic arms 40*a-d* and their instruments 50 are calibrated while being coupled to the control tower 20. Thus, the primary power mode is automatically enabled upon connecting the carts 60*a-d* to the control tower 20.

At step 202, the system 10 continuously monitors GUI or other user interface devices for a user request to switch to a battery power mode, e.g., to move the carts 60*a-d* to a new location in the operating room.

At step 204, the system 10 determines if a request is received. If not, the system 10 continues to monitor user input. If a request is received, at step 206 the system 10 determines whether the battery 108 has sufficient minimum charge allotted for the maneuvering of the carts 60*a-d* based on the data provided by the battery charger circuit 110. The charge level and/or the allotted time may be user adjustable values for the system 10. If there is sufficient charge, at step 208, the power delivery system 100 switches to the battery power mode. If there the remaining charge is insufficient, then the power delivery system 100, at step 209, outputs an alert indicating that the charge level is too low and/or to reconnect the cart via the cable to the control tower 20 as soon as possible. In embodiments, a remaining time countdown may be displayed on any of the displays of the system 10.

In addition to user-requested power mode switching, the method also includes automatic switching based on detection of cable disconnection. As described above with respect to FIG. 7, the connection status of the cables is monitored at step 210, which may be accomplished using the cable detection circuit 120. In embodiments, the power delivery system 100 may also be used to determine the presence of the cables by monitoring the supplied voltage, e.g., dropping to zero. At step 212, the system 10 determines whether the cable is disconnected, which may be done: at the cart 60 by failure to detect the signal 121 from the control tower 20; at the control tower 20 by failure to detect the looped back signal 121 from one of the carts 60*a-d;* and/or at the cart 60 by detecting a change in the properties of the DC voltage signal supplied by the control tower 20. If the cable is detected as being disconnected, the system 10 proceeds to steps 206 and 208 as described above. If the cable is connected, the system 10 continues to monitor the cable connection status.

The present disclosure allows for setting up a surgical robotic system without positioning multiple carts prior to starting other components of the system, i.e., control tower, surgeon console, etc. The carts may be initially connected to the control tower for calibration and then disconnected to move the carts to the desired location. After the carts are placed the cables may be reconnected without affecting system startup. The present disclosure also allows the carts that are already in position and ready for surgery to be unplugged from their cables and repositioned without the cables causing interference. Thus, delays caused by cart placement and movement are greatly reduced.

It will be understood that various modifications may be made to the embodiments disclosed herein. Therefore, the above description should not be construed as limiting, but merely as exemplifications of various embodiments. Those skilled in the art will envision other modifications within the scope and spirit of the claims appended thereto.

What is claimed is:

1. A power delivery system for a surgical robotic movable cart, the power delivery system comprising:

a power input configured to receive a first DC electrical signal;

a first voltage sense and control circuit coupled to the power input and operable in a primary power mode to output the first DC electrical signal;

a battery configured to output a second DC electrical signal;

a battery charging circuit configured to receive the first DC electrical signal and to charge the battery;

a second voltage sense and control circuit coupled to the battery and operable in a battery power mode to output the second DC electrical signal;

a sharing circuit configured to output at least one of the first DC electrical signal from the first voltage sense and control circuit or the second DC electrical signal from the second voltage sense and control circuit; and a cable detection circuit including:

a detection signal source coupled to a first end of a cable configured to generate a detection signal;

a first cable monitor coupled to a second end of the cable and configured to monitor the detection signal; and a second cable monitor coupled to the first end of the cable, the second cable monitor configured to monitor the detection signal, wherein the cable detection circuit is configured to determine cable disconnection based on at least one of the first cable monitor or the second cable monitor failing to receive the detection signal, wherein the sharing circuit is controlled to switch between the first DC electrical signal and the second DC electrical signal based on at least one of (i) detection of a cable disconnection or (ii) a state of charge of the battery.

2. The power delivery system according to claim 1, wherein the first and second voltage sense and control circuits are configured to receive a user input to switch between the primary power mode and the battery power mode.

3. The power delivery system according to claim 1, wherein the first and second voltage sense and control circuits are configured to switch from the primary power mode to the battery power mode in response to detection of the cable disconnection.

4. The power delivery system according to claim 1, wherein the second voltage sense and control circuit is configured to monitor the state of charge of the battery and to enable a switch from the primary power mode to the battery power mode in response to the state of charge being above a state of charge threshold.

5. A surgical robotic system comprising:
   a control tower including a DC power source; and
   a movable cart supporting a robotic arm having at least one of a camera or an instrument, wherein the movable cart includes a power delivery system including:
   a power input configured to receive a first DC electrical signal from the DC power source;
   a first voltage sense and control circuit coupled to the power input and operable in a primary power mode to output the first DC electrical signal;
   a battery configured to output a second DC electrical signal;
   a battery charging circuit configured to receive the first DC electrical signal and to charge the battery;
   a second voltage sense and control circuit coupled to the battery and operable in a battery power mode to output the second DC electrical signal; and
   a sharing circuit configured to output at least one of the first DC electrical signal from the first voltage sense and control circuit or the second DC electrical signal from the second voltage sense and control circuit to power the movable cart; and
   a cable detection circuit including:
      a detection signal source disposed at the control tower, the detection signal source configured to generate a detection signal;
      a first cable monitor disposed at the movable cart, the first cable monitor configured to monitor the detection signal; and
      a second cable monitor disposed at the control tower, the second cable monitor configured to monitor the detection signal returned from the movable cart, wherein the cable detection circuit is configured to determine cable disconnection based on at least one of the first cable monitor or the second cable monitor failing to receive the detection signal,
   wherein the sharing circuit is controlled to switch between the first DC electrical signal and the second DC electrical signal based on at least one of (i) detection of a cable disconnection or (ii) the state of charge of the battery.

6. The surgical robotic system according to claim 5, wherein the first and second voltage sense and control circuits are configured to receive a user input to switch between the primary power mode and the battery power mode.

7. The surgical robotic system according to claim 6, further comprising a display configured to output a graphical user interface for receiving the user input.

8. The surgical robotic system according to claim 5, wherein the first and second voltage sense and control circuits are configured to switch from the primary power mode to the battery power mode in response to detection of cable disconnection.

9. The surgical robotic system according to claim 5, wherein the second voltage sense and control circuit is configured to monitor a state of charge of the battery and to enable a switch from the primary power mode to the battery power mode in response to the state of charge being above a state of charge threshold.

10. A method for controlling power delivery to a surgical robotic movable cart, the method comprising:
   supplying a first DC electrical signal from a DC power source housed in a control tower to a power input of a movable cart;
   outputting the first DC electrical signal through a first voltage sense and control circuit operable in a primary power mode;
   receiving the first DC electrical signal at a battery charging circuit and charging a battery using the first DC electrical signal;
   supplying a second DC electrical signal from the battery;
   outputting the second DC electrical signal through a second voltage sense and control circuit operable in a battery power mode;
   outputting through a sharing circuit at least one of the first DC electrical signal from the first voltage sense and control circuit or the second DC electrical signal from the second voltage sense and control circuit to power the movable cart; and
   monitoring a connection of the power input to a cable at a cable detection circuit, including:
      generating a detection signal at a detection signal source disposed at the control tower;
      monitoring the detection signal at a first cable monitor disposed at the movable cart;
      monitoring the detection signal returned from the movable cart at a second cable monitor disposed at the control tower;
      determining, at the cable detection circuit, cable disconnection based on at least one of the first cable monitor or the second cable monitor failing to receive the detection signal; and
   switching from the primary power mode to the battery power mode in response to detection of a cable disconnection.

11. The method according to claim 10, further comprising:
   receiving a user input at the first and second voltage sense and control circuits to switch between the primary power mode and the battery power mode.

12. The method according to claim 11, wherein receiving the user input is performed through a graphical user interface output on a display.

13. The method according to claim 10, further comprising:
   monitoring a state of charge of the battery; and
   enabling a switch from the primary power mode to the battery power mode in response to the state of charge being above a state of charge threshold.

* * * * *